United States Patent
Kellerman et al.

(10) Patent No.: US 11,564,728 B1
(45) Date of Patent: Jan. 31, 2023

(54) SYSTEMS AND METHODS FOR PERCUTANEOUS ACCESS, FORMATION, AND MAINTENANCE OF ARTERIOVENOUS FISTULAS

(71) Applicant: Avenu Medical, Inc., San Juan Capistrano, CA (US)

(72) Inventors: Brad M. Kellerman, Escondido, CA (US); Gene B. Reu, San Clemente, CA (US); Mark A. Ritchart, Dana Point, CA (US); Jeffrey E. Hull, Midlothian, VA (US)

(73) Assignee: AVENU MEDICAL, INC., San Juan Capistrano, CA (US)

( * ) Notice: Subject to any disclaimer, the term of this patent is extended or adjusted under 35 U.S.C. 154(b) by 626 days.

(21) Appl. No.: 16/219,759

(22) Filed: Dec. 13, 2018

Related U.S. Application Data

(60) Provisional application No. 62/607,894, filed on Dec. 19, 2017, provisional application No. 62/598,930, filed on Dec. 14, 2017.

(51) Int. Cl.
*A61B 18/08* (2006.01)
*A61B 17/11* (2006.01)
*A61B 18/00* (2006.01)

(52) U.S. Cl.
CPC ..... *A61B 18/082* (2013.01); *A61B 2017/1107* (2013.01); *A61B 2018/0063* (2013.01); *A61B 2018/00404* (2013.01); *A61B 2018/00619* (2013.01)

(58) Field of Classification Search
CPC .......... A61B 17/11; A61B 2018/00619; A61B 2018/0063; A61B 17/12022; A61B 17/1204; A61B 17/12045; A61B 2017/12127; A61B 2017/12136; A61B 2017/1214; A61B 2017/12145; A61B 2017/12154; A61B 2017/12159; A61B 2017/12163; A61B 2017/12168; A61B 2017/12172; A61B 2017/12177; A61B 2017/1107; A61B 2018/00404; A61B 2018/00339; A61B 18/082

See application file for complete search history.

(56) References Cited

U.S. PATENT DOCUMENTS

| 4,470,415 | A | * | 9/1984 | Wozniak ................ A61B 17/11 29/447 |
| 6,464,665 | B1 | | 10/2002 | Heuser |
| 8,062,321 | B2 | | 11/2011 | Heuser et al. |
| 9,259,340 | B2 | | 2/2016 | Heuser et al. |
| 9,301,830 | B2 | | 4/2016 | Heuser et al. |
| 9,439,710 | B2 | * | 9/2016 | Reu ...................... A61B 18/082 |

(Continued)

OTHER PUBLICATIONS

Spivack et al., Mapping of Superficial Extremity Veins: Normal Diameters and Trends in a Vascular Patient-Population, 2011, p. 190 (Year: 2011).*

(Continued)

*Primary Examiner* — Linda C Dvorak
*Assistant Examiner* — Nicholas S Borsch
(74) *Attorney, Agent, or Firm* — Stinson LLP

(57) ABSTRACT

Methods for creating and maintaining an anastomosis between two adjacent blood vessels using percutaneous techniques, for use in hemodialysis procedures are disclosed and described.

20 Claims, 10 Drawing Sheets

(56) References Cited

U.S. PATENT DOCUMENTS

| | | | |
|---|---|---|---|
| 9,452,015 B2 | 9/2016 | Kellerman et al. | |
| 9,474,562 B2 | 10/2016 | Kellerman et al. | |
| 9,522,016 B2 | 12/2016 | Kellerman et al. | |
| 2006/0271107 A1* | 11/2006 | Harrison | A61B 17/8076 606/237 |
| 2007/0203515 A1 | 8/2007 | Heuser et al. | |
| 2008/0171944 A1* | 7/2008 | Brenneman | A61B 17/11 600/509 |
| 2011/0306959 A1* | 12/2011 | Kellerman | A61B 18/1492 606/28 |
| 2014/0107642 A1* | 4/2014 | Rios | A61B 17/3478 606/41 |
| 2016/0000985 A1* | 1/2016 | Consigny | A61M 1/3655 604/6.09 |
| 2016/0058452 A1* | 3/2016 | Brenneman | A61B 17/11 606/153 |

OTHER PUBLICATIONS

Proximal radial artery proof of date (Year: 2021).*
Kamata et al, An unusual case of arteriovenous fistula related venous hypertension: sonographic detection of a culprit perforating vein with movie and compact review, 2016, Biomed Central, pp. 1-5 (Year: 2016).*
An unusual case proof of date (Year: 2021).*
Jennings et al, Proximal radial artery arteriovenous fistula for hemodialysis vascular access, Sep. 11, 2017, Journal of Vascular Surgery, pp. 244-253 (Year: 2017).*

* cited by examiner

SYSTEMS AND METHODS FOR PERCUTANEOUS ACCESS, FORMATION, AND MAINTENANCE OF ARTERIOVENOUS FISTULAS

This application claims the benefit under 35 U.S.C. 119(e) of the filing date of Provisional U.S. Application Ser. No. 62/607,894, entitled Systems and Methods for Percutaneous Access, Formation, and Maintenance of Arteriovenous Fistulas, filed on Dec. 19, 2017, and also of Provisional U.S. Application Ser. No. 62/598,930, entitled Systems and Methods for Percutaneous Access, Formation, and Maintenance of Arteriovenous Fistulas, filed on Dec. 14, 2017. Both of these prior, commonly assigned applications are herein expressly incorporated by reference, in their entirety.

BACKGROUND OF THE INVENTION

In the body, various fluids are transported through conduits throughout the organism to perform various essential functions. Blood vessels, arteries, veins, and capillaries carry blood throughout the body, carrying nutrients and waste products to different organs and tissues for processing. Bile ducts carry bile from the liver to the duodenum. Ureters carry urine from the kidneys to the bladder. The intestines carry nutrients and waste products from the mouth to the anus.

In medical practice, there is often a need to connect conduits to one another or to a replacement conduit to treat disease or dysfunction of the existing conduits. The connection created between conduits is called an anastomosis.

In blood vessels, anastomoses are made between veins and arteries, arteries and arteries, or veins and veins. The purpose of these connections is to create either a high flow connection, or fistula, between an artery and a vein, or to carry blood around an obstruction in a replacement conduit, or bypass. The conduit for a bypass is a vein, artery, or prosthetic graft.

An anastomosis is created during surgery by bringing two vessels or a conduit into direct contact. The vessels are joined together with suture or clips. The anastomosis can be end-to-end, end-to-side, or side-to-side. In blood vessels, the anastomosis is elliptical in shape and is most commonly sewn by hand with a continuous suture. Other methods for anastomosis creation have been used including carbon dioxide laser approaches and a number of methods using various connected prostheses, clips, and stents.

An arterio-venous fistula (AVF) is created by connecting an artery to a vein, and to create a leak-free blood flow path between them. This type of connection is used for hemodialysis, to increase exercise tolerance, to keep an artery or vein open, or to provide reliable access for chemotherapy.

An alternative is to connect a prosthetic graft from an artery to a vein for the same purpose of creating a high flow connection between artery and vein. This is called an arterio-venous graft, and requires two anastomoses. One is between artery and graft, and the second is between graft and vein.

A bypass is similar to an arteriovenous graft. To bypass an obstruction, two anastomoses and a conduit are required. A proximal anastomosis is created from a blood vessel to a conduit. The conduit extends around the obstruction, and a second distal anastomosis is created between the conduit and vessel beyond the obstruction.

As noted above, in current medical practice, it is desirable to connect arteries to veins to create a fistula for the purpose of hemodialysis. The process of hemodialysis requires the removal of blood from the body at a rapid rate, passing the blood through a dialysis machine, and returning the blood to the body. The access to the blood circulation is achieved with 1) catheters placed in large veins, 2) prosthetic grafts attached to an artery and a vein, or 3) a fistula where an artery is attached directly to the vein.

Hemodialysis is required by patients with kidney failure. A fistula using native blood vessels is one way to create high blood flow. The fistula provides a high flow of blood that can be withdrawn from the body into a dialysis machine to remove waste products and then returned to the body. The blood is withdrawn through a large access needle near the artery and returned to the fistula through a second large return needle. These fistulas are typically created in the forearm, upper arm, less frequently in the thigh, and in rare cases, elsewhere in the body. It is important that the fistula be able to achieve a flow rate of 500 ml per minute or greater in order for the vein to mature or grow. The vein is considered mature once it reaches >4 mm and can be accessed with a large needle. The segment of vein in which the fistula is created needs to be long enough (>6 cm) to allow adequate separation of the access and return needle to prevent recirculation of dialyzed and non-dialyzed blood between the needles inserted in the fistula.

Fistulas are created in anesthetized patients by carefully dissecting an artery and vein from their surrounding tissue, and sewing the vessels together with fine suture or clips. The connection thus created is an anastomosis. It is highly desirable to be able to make the anastomosis quickly, reliably, with less dissection, and with less pain. It is important that the anastomosis is the correct size, is smooth, and that the artery and vein are not twisted.

SUMMARY OF THE INVENTION

In one aspect of the invention, there is described a method for creating an anastomosis between first and second blood vessels which comprises a step of identifying an anatomical location in a patient as a procedural site, wherein a distance between the first blood vessel and the second blood vessel is approximately 2 mm or less, which can be accessed from the deep communicating (perforating) vein (DCV), and from which at least one superficial outflow vessel has a diameter of at least 2 mm. Further steps in the method comprise a step of creating an opening through a first blood vessel wall and an adjacent second blood vessel wall, the opening comprising a communicating opening between the first blood vessel and the second blood vessel, and dilating the communicating opening to form a fistula.

The identifying step may further comprise selecting the DCV as the first blood vessel, and selecting the radial artery or the brachial artery as the second blood vessel. Alternatively, the identifying step may comprise: a) selecting the radial vein as the first blood vessel and the radial artery as the second blood vessel, b) selecting the deep ulnar vein as the first blood vessel and the ulnar artery as the second blood vessel, c) selecting the median cubital vein as the first blood vessel and the brachial artery as the second blood vessel, d) selecting the median vein as the first blood vessel and the radial artery as the second blood vessel, e) selecting the deep brachial vein as the first blood vessel and the brachial artery as the second blood vessel, or f) selecting the distal cephalic vein as the first blood vessel and the radial artery as the second blood vessel. These alternative selections are not exhaustive, of course.

A further method step may comprise dilating the first blood vessel before the step of creating an opening. This dilating step is performed using one of a brachial plexus block (BPB), axillary block, or a vasodilator drug.

The step of creating an opening is performed, in representative approaches, using a needle. The step of dilating the communicating opening is performed using a dilator. In representative approaches, the dilator is expandable to a larger peripheral size in order to effectively dilate the communicating opening. For example, the dilator may comprise an expandable balloon.

A further method step is a step of removing tissue to enlarge the communicating opening. The method may further comprise a step of applying heat to tissue surrounding the communicating opening to seal or weld the tissue. The method further comprises a step of measuring blood flow volume to determine blood flow volume through the communicating opening, and dilating the communicating opening if the determined blood flow volume is below a predetermined level. In one particular approach, the predetermined blood flow volume level is approximately 500 ml/min. The dilating step after determining the blood flow volume through the communicating opening may be performed using an inflatable balloon.

In another aspect of the invention, there is described a method for creating an anastomosis between first and second blood vessels, which comprises identifying a procedural site for creating the anastomosis, having adjacent first and second blood vessels, creating an opening through a first blood vessel wall and an adjacent second blood vessel wall, the opening comprising a communicating opening between the first blood vessel and the second blood vessel, determining blood flow volume through the communicating opening, and dilating the communicating opening if the determined blood flow volume is below a predetermined level.

The predetermined blood flow volume level is approximately 500 ml/min in one particular approach. The dilating step after determining the blood flow volume may be performed using an inflatable balloon. After the first dilating step, the method may comprise a second step of determining the blood flow volume through the communicating opening after the dilating step to ensure that the first dilating step was effective. If it was not, the method may comprise a second step of dilating the communicating opening if the determined blood flow volume obtained during the second step of determining the blood flow volume is below the predetermined blood flow volume level. The second dilating step will typically be performed using a larger dilator or longer inflation time than was used to perform the first dilating step, to ensure an effective anastomosis.

The foregoing method may further comprise a step of evaluating secondary outflow vessels downstream from the communicating opening for suitability of use as a future dialysis access point and creating a flow restriction in one of the secondary outflow vessels.

In yet another aspect of the invention, there is disclosed a method for creating an anastomosis between first and second blood vessels, which comprises steps of identifying a procedural site for creating the anastomosis, having adjacent first and second blood vessels, creating an opening at the procedural site through a first blood vessel wall and an adjacent second blood vessel wall, advancing a catheter having a proximal portion and a distal portion over a guidewire to the procedural site, advancing the distal catheter portion through the opening into the second blood vessel, and retracting the distal portion so that a proximal face thereon contacts tissue on the second blood vessel wall. Further steps include contacting tissue on the first blood vessel wall with a distal face on the proximal portion, thereby capturing tissue between the proximal and distal faces, measuring a distance between the proximal and distal faces to thereby determine a thickness of the tissue captured between the proximal and distal faces, releasing and recapturing the tissue if the determined thickness of the captured tissue is not within a predetermined range, applying energy to a heating surface on one or both of the proximal and distal faces to heat the captured tissue to a prescribed temperature, and stopping the application of energy to the heating surface when a measured distance between the distal and proximal faces reaches a desired level. In a particular approach, the predetermined range of the thickness of the captured tissue is 0.1 mm-0.6 mm. The desired level is reached when the distal and proximal faces are in contact with one another.

The method may, in some circumstances, further comprise a step of advancing a sheath having a dilator to the procedural site over a guidewire prior to the catheter advancing step, the sheath advancing step comprising rotating the sheath as it is advanced over the guidewire to release any tissue that may be caught between the guidewire and the sheath or guidewire. This method comprises further advancing the dilator through the opening to dilate the opening. The applying energy step may applying short pulses of direct current energy to the heating surface. The applied heating pulses may range from 0.5 to 3 seconds in length, while the prescribed temperature may fall within a range of approximately 200 to 700 degrees F.

After the stopping step, the inventive method may comprise applying a further pulse of energy to heat tissue surrounding the catheter and thereby release any tissue sticking to the catheter so that the catheter may be withdrawn.

The invention, together with additional features and advantages thereof, may best be understood by referencing the following description in conjunction with the accompanying specifications.

DETAILED DESCRIPTION OF THE INVENTION

Notation and Nomenclature

Figure 1:
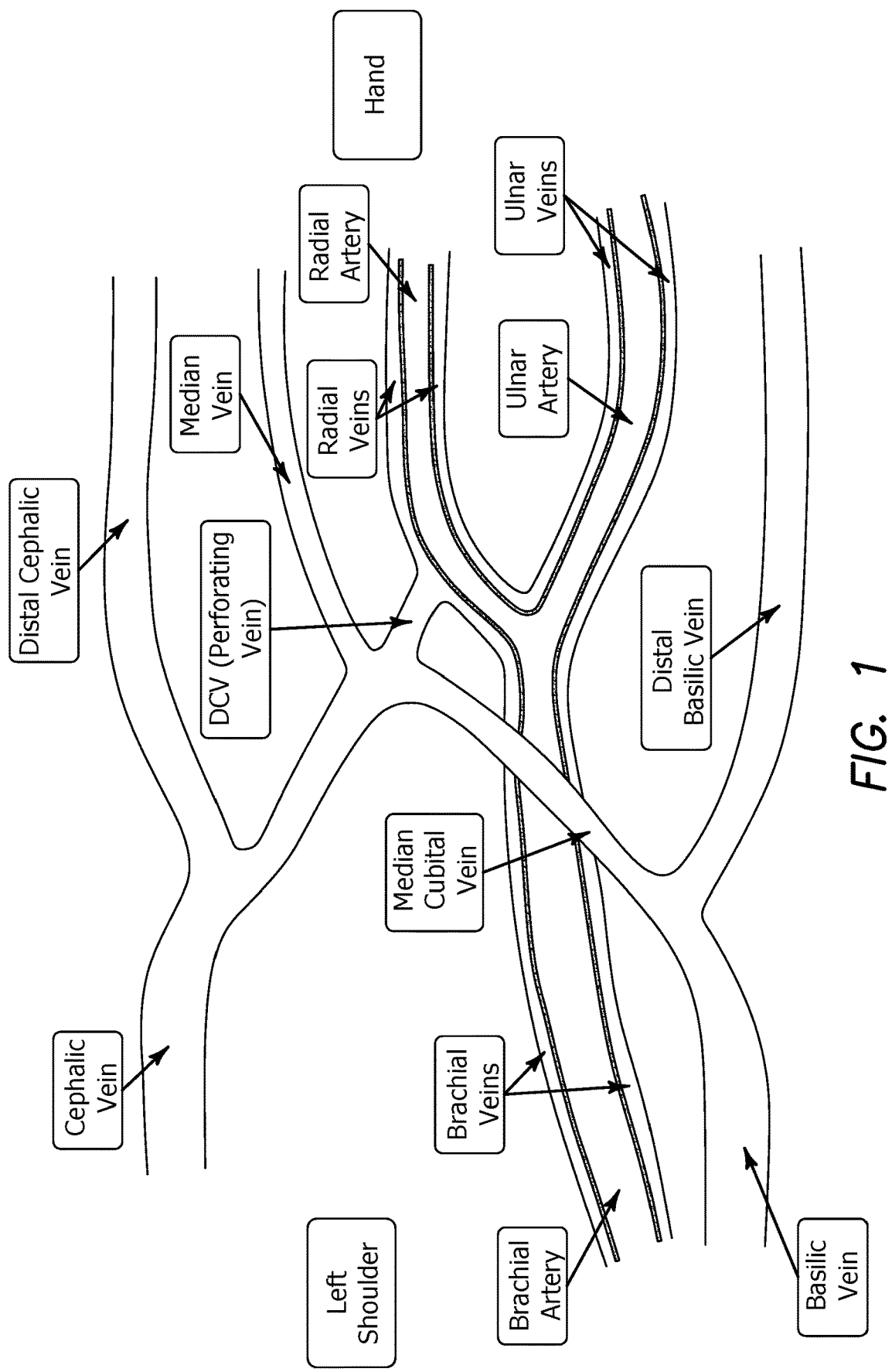
FIG. 1 is an anatomical schematic rendering of the vasculature of a representative patient between the left shoulder (left side of drawing figure) and the thank (right side of drawing figure)

Certain terms are used throughout the following description and claims to refer to particular system components. As one skilled in the art will appreciate, companies that design and manufacture medical devices may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ."

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent application and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

The technology disclosed herein would have a broad application in vessel surgery for humans and other mammals. This includes surgery of ducts, ureters, arteries, veins, grafts, or any other tubular structure that transports material. Some of these procedures include, but are not limited to, artery to venous fistula creation, vascular repair, coronary artery bypass graft surgery, femoral popliteal bypass, transjugular intrahepatic portosystemic shunt, splenorenal shunt, or a mesocaval shunt.

Referring now more particularly to the drawings, there is illustrated in FIG. 1, schematically, an anatomical rendering of the vasculature of a representative patient between the left shoulder (left side of drawing figure) and the hand (right side of drawing figure). This rendering is representative only, for the purpose of illustrating elements of the inventive methods and systems discussed herein.

An initial step in the creation of an anastomosis in accordance with the methods disclosed in this application is to conduct initial patient screening, for the purpose of ascertaining the patient's suitability for the procedure, and to select the preferred procedural site. Specifically, the practitioner evaluates target procedural sites to identify anatomical locations where the artery and vein are within approximately 2 mm proximity to one another, typically using ultrasound imaging, or other suitable imaging modalities, such as angiography, MRI or CT imaging. An identified anatomical location can be accessed from the deep communicating (perforating) vein (DCV) in the elbow region. Specific locations may include the perforating vein to the radial artery, the perforating vein to the brachial artery, the radial vein to the radial artery, the deep ulnar vein to the ulnar artery, the median cubital vein to the brachial artery, the distal cephalic vein to the radial artery, and the median vein to the radial artery. Alternatively, a possible location is between the deep brachial vein and the brachial artery. These potential procedural site locations are all illustrated in FIG. 1. The measured diameter of the target vessels, distance between the target vessels, and abnormalities, such as calcification, of the target vessels are all factors in determining the most appropriate procedural site.

It is also important to evaluate the superficial outflow vessels for the selected site. Ultrasound or other suitable imaging technologies may be used to measure the diameter of the outflow vessel (at least one vein should be greater than 2 mm in diameter), to ascertain that the outflow vessel is free from stenosis, thrombosis or clot, and also to ascertain that the outflow vessel wall is not thickened or diseased, and thus capable of being dilated with a tourniquet.

The inventors have found that because the DCV typically connects to multiple outflow vessels, it provides multiple additional options for dialysis access. It also preserves the vein because there are multiple flow conduits.

Once the patient has been screened, and a suitable procedural site selected, the anastomosis creation procedure can begin. A first step in the creation of the anastomosis is to dilate the access vessel. First, vasodilation of the access vessel is desired to maintain the lumen diameter and improve delivery of the access needle to the target anastomosis site. This may be achieved by administration of a brachial plexus block (BPB) or axillary block which temporarily disables the sympathetic nervous system in the arm and causes the target vessels to dilate. Alternatively, an ipsilateral IV may be initiated in a suitable location, such as the hand, to administer a continuous drip of a vasodilator drug, such as verapamil and nitroglycerin, to the vessels. Additionally, a vasodilator may be injected directly into the vein at the initial venous access site. Also, a tourniquet may be applied to the upper arm to increase pressure in the venous system and provide vasodilation. It should be noted that the above steps may be performed individually, or may all be done together, as none of the foregoing steps preclude other steps and none of the steps, individually, are absolutely required.

Under ultrasound guidance, the median cubital vein is punctured using a needle (not shown) near the bifurcation of the deep communicating vein 24. The access location is such that the needle is pointing down the axis of the perforating vein. The superficial location provides easy needle access and good visualization under ultrasound.

A vasodilator is then injected into the vein to promote additional local vasodilation and prevent vasoconstriction and subsequent occlusion.

According to one aspect of the inventive method, a guidewire (not shown) is inserted through the needle and advanced down the perforating vein to the target anastomosis site. Under ultrasound guidance, the needle is kept centered in the vessel and advanced down the perforating vein, over the guidewire, to the target anastomosis site. If resistance is felt on the needle, the needle is retracted slightly and/or rotated to release any tissue that may be caught on the distal tip of the needle and help keep it centered in the vein lumen over the guidewire.

Figure 2:
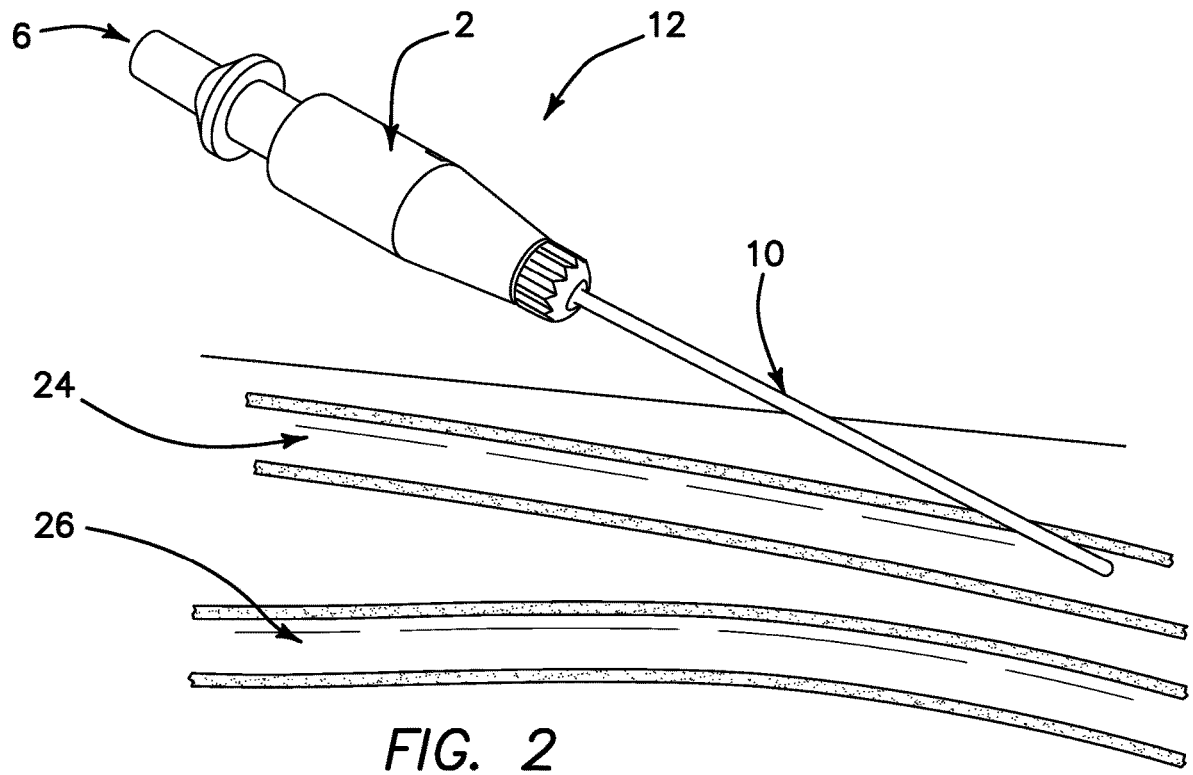
FIG. 2 is a schematic view illustrating a device which may be used in the inventive methods being inserted directly into a first blood vessel, which lies adjacent to a second blood vessel.

According to an alternative aspect of the inventive method, a guidewire (not shown) is inserted through the needle and advanced down the perforating vein to the target anastomosis site. The needle is then removed. As shown in FIG. 2, a body shaft 10 is then inserted over the guidewire (not shown) into the vein (first blood vessel) 24. The distal end 32 thereof (FIG. 3) lies within the blood flow passage of the vein 24. The device illustrated herein is disclosed in more detail in U.S. Pat. No. 9,522,016, commonly assigned with the present application and expressly incorporated by reference herein.

Figure 3:
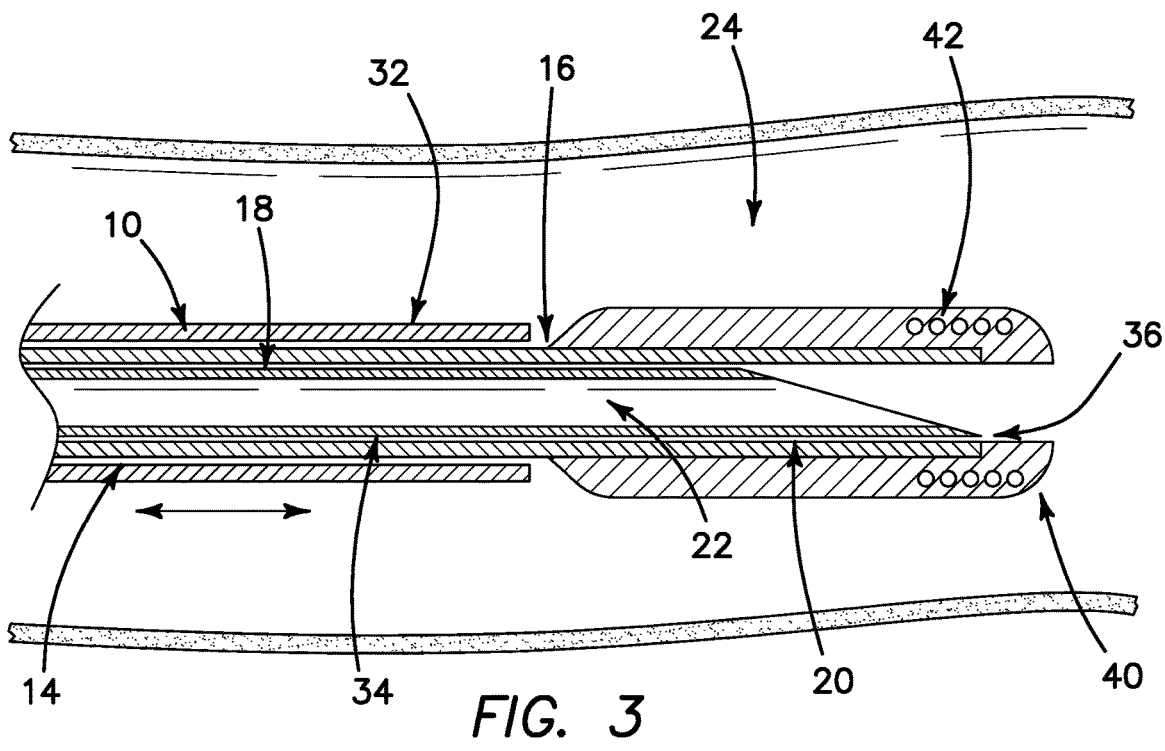
FIG. 3 is a view of one representative embodiment of a distal end of a device like that shown in FIG. 1, disposed in the first blood vessel.

It should be noted that the aforementioned guidewire for guiding the needle is optional. Alternatively, the needle may simply be advanced freely to the procedural site, as shown in FIG. 3, using imaging guidance. In such case, the needle still may be retracted or rotated slightly as resistance is felt, in order to release caught tissue and keep the needle on track.

With further reference now to FIG. 3, a needle 20 comprises a needle shaft 34, lumen 22, and a distal tip 36, and can be adjustably oriented axially within the secondary lumen 18 of a needle guide 16, and lumen 22 provides an externally communicating passage. In this embodiment, a distal end 40 of the needle guide 16 comprises a blunt large diameter atraumatic tip, comprised of a polymer material, having a rounded distal edge. This distal end 40 also has features that make it visible under different imaging techniques, such as ultrasound, fluoroscopy, CT, or MRI. There is a coil 42 constructed of a radiopaque material, embedded in the polymer distal end 40. Small particles of air or other radiopaque materials known to those skilled in the art may also be used to increase the radiopacity of the end 40.

Figure 4:
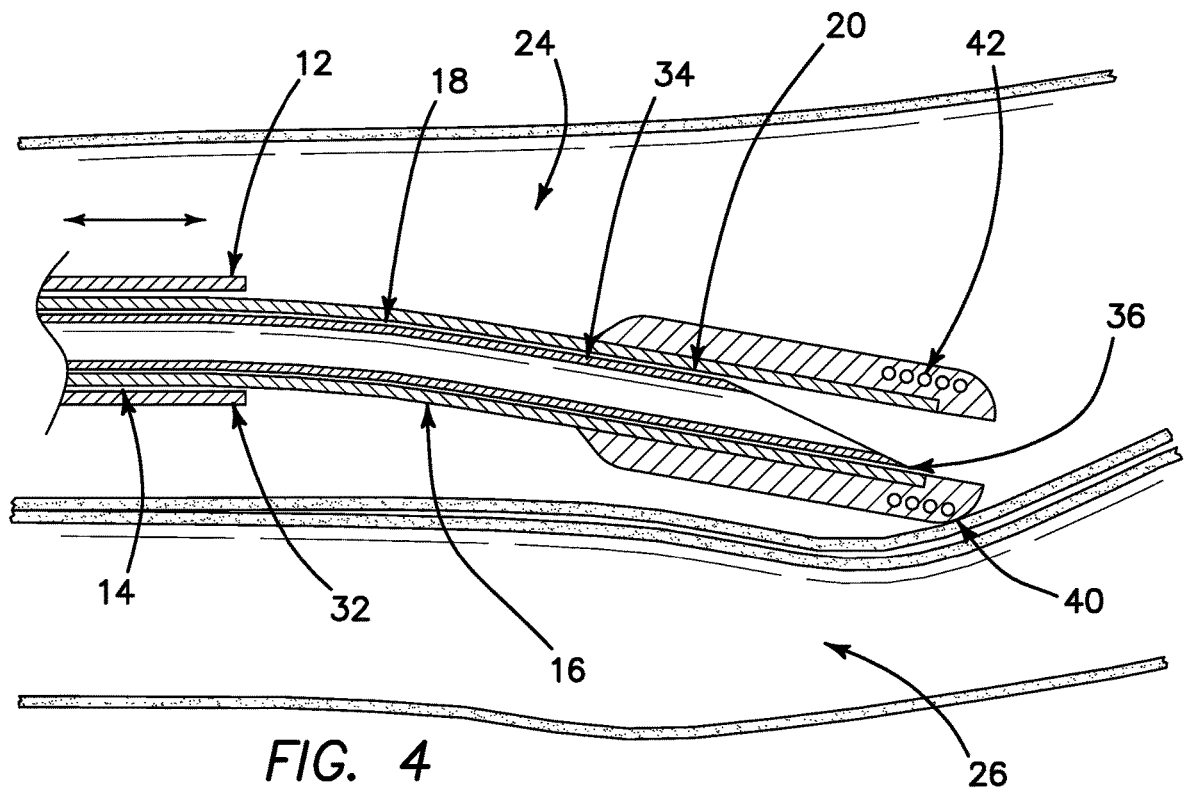
FIG. 4 is a view illustrating a blunt distal end of the device of FIG. 3 contacting an inner wall of the first blood vessel and pushing it into desired engagement with the adjacent wall of the second blood vessel.

Referring to FIG. 4, the blunt distal end 40 is manipulated to contact an inner wall of the vein 24 and to push it into desired engagement with the adjacent wall of an adjacent artery (second blood vessel) 26. The position of desired engagement is arranged to optimize the piercing step to be next described. Up to this point, the needle 20 is retracted within the needle guide 16, but now the distal tip 36 of the needle 20 may be longitudinally extended with respect to the needle guide 16. An advantage of this approach is that the beveled needle tip is sheathed during the advancement of the needle through the vein, so that the tip of the needle is atraumatic and can track down the vein toward the anastomosis site without catching on the vessel wall.

Figure 5:
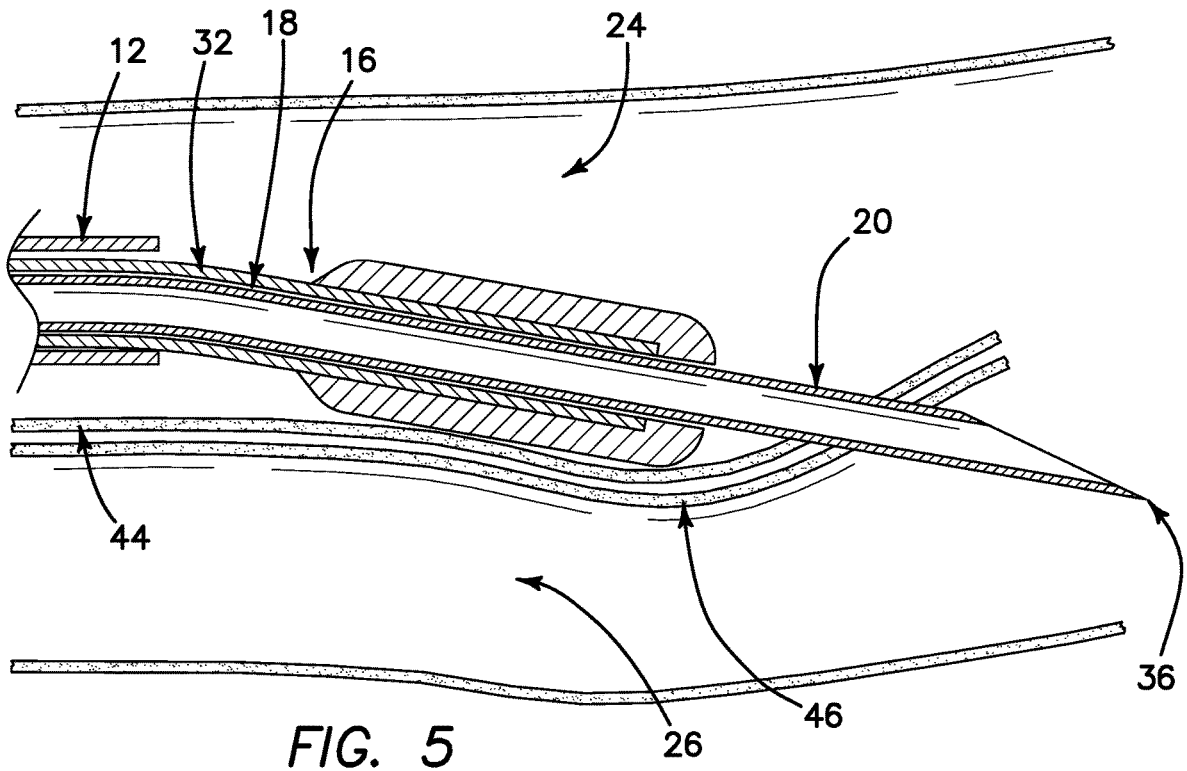
FIG. 5 is a schematic representation showing a needle advanced distally from the device distal end through the adjacent vessel walls and into the second blood vessel.

At this juncture, under either of the aforementioned alternative approaches for advancing the needle, the guidewire is retracted to expose the beveled tip of the needle. As shown, for example, in FIG. 5, under ultrasound visualization, or other suitable direct imaging guidance, the needle hub is positioned such that the tip is aimed at the center of the artery 26 and the needle 20 is advanced forwardly to penetrate from the vein 24 through the vein (first blood vessel) wall 44 into the artery 26 through the artery (second blood vessel) wall 46. It is important at this point to verify, using direct imaging guidance, complete penetration without extending beyond the flow passage of artery 26. Thus, as the needle moves, the ultrasound transducer is moved in unison to maintain visualization of the needle tip. The practitioner may also verify acceptable penetration through direct visualization of blood that flows through lumen 22 and exits through an aperture 6 of the handle 2 as shown in FIG. 2.

In an alternative approach, to more accurately puncture the artery from the vein, an Intravascular Ultrasound (IVUS) catheter is positioned in the adjacent artery 26 at the target anastomosis location. The needle guidewire is retracted to expose the beveled tip of the needle. The needle is torqued to aim the needle tip toward the artery. The position of the needle tip relative to the artery is visualized using IVUS.

Figure 6:
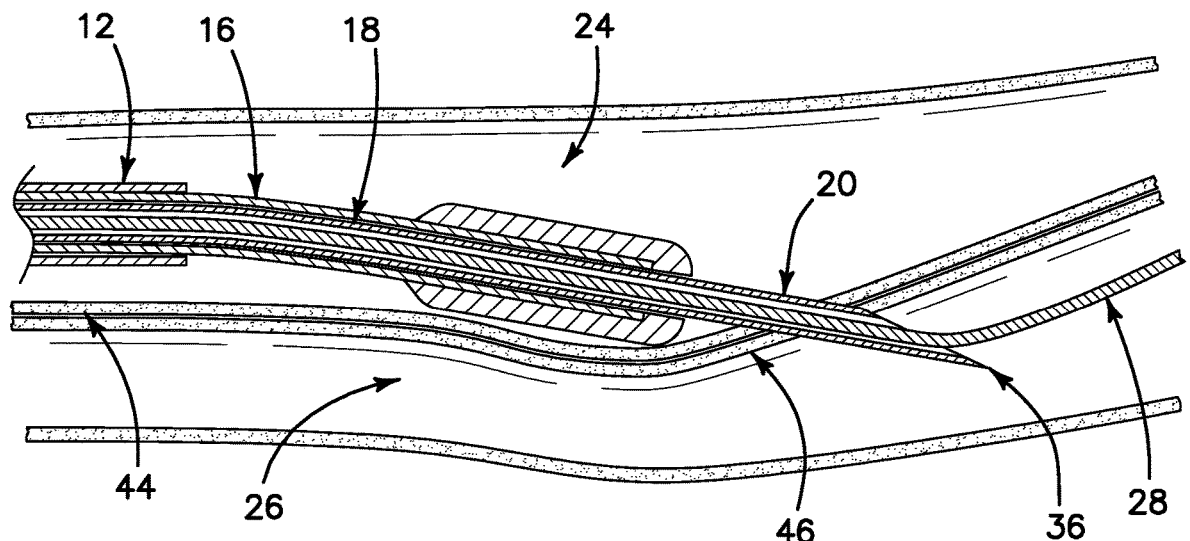
FIG. 6 is a schematic representation similar to FIG. 5, wherein a guidewire has been advanced into the second blood vessel through the needle.

With reference now to FIG. 6, once penetration from the perforating vein 24 to the artery 26 has been achieved by the needle 20, a guidewire 28, preferably having a diameter of 0.014" or less, is advanced through the aperture 6 of the handle 2 until the guidewire is positioned in the blood flow path of the artery 26 sufficiently to allow the needle 20 to be removed while retaining the guidewire's position in artery 26.

Figure 7:
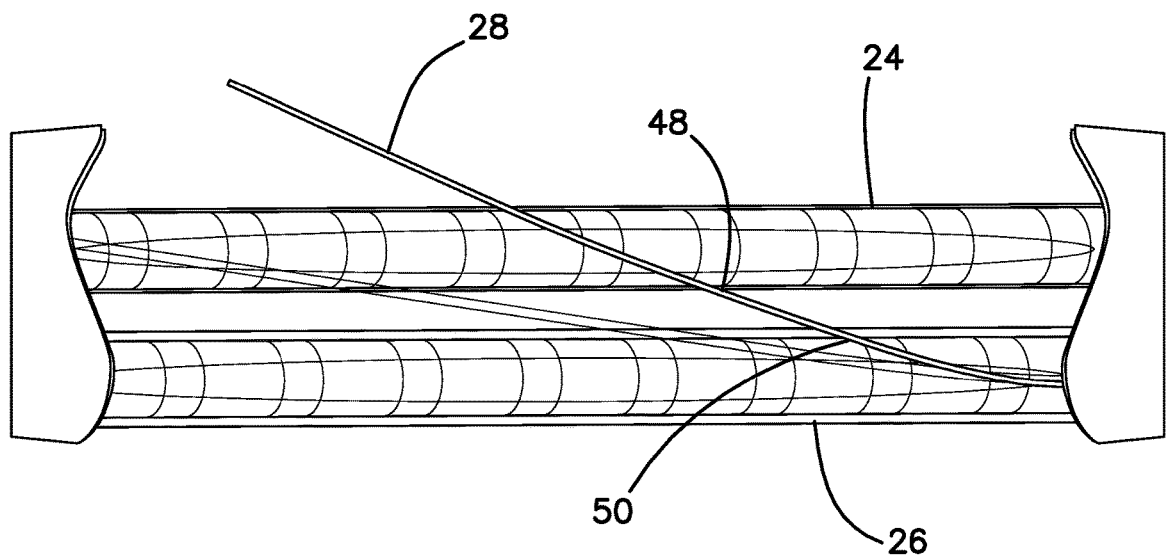
FIG. 7 is a schematic view wherein the device has been withdrawn from the procedural site, leaving the guidewire in place between the first and second blood vessels.

Now referring to FIG. 7, once the guidewire 28 is sufficiently in position as previously described, the practitioner withdraws the device 10 completely from the body, thus leaving the guidewire in the desired position and crossing from vein 24 to artery 26.

Figure 8:
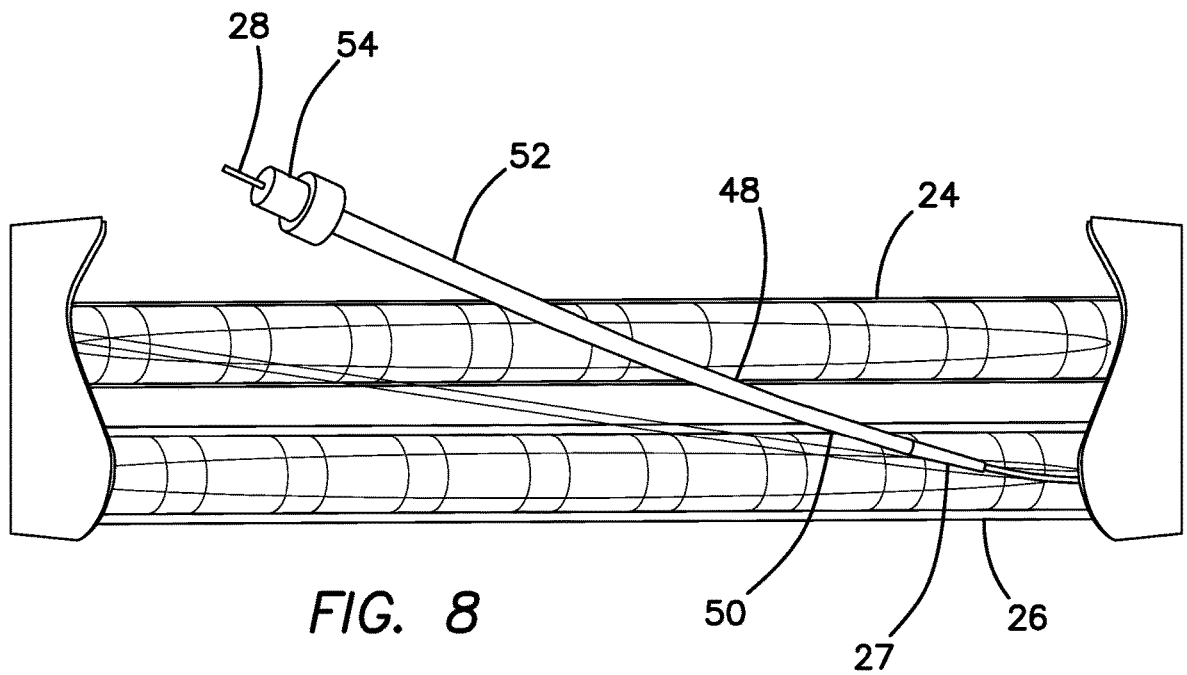
FIG. 8 is a schematic view similar to FIG. 7, wherein a second device or sheath has been advanced into the blood vessels over the guidewire, according to one representative embodiment.
Figure 9:
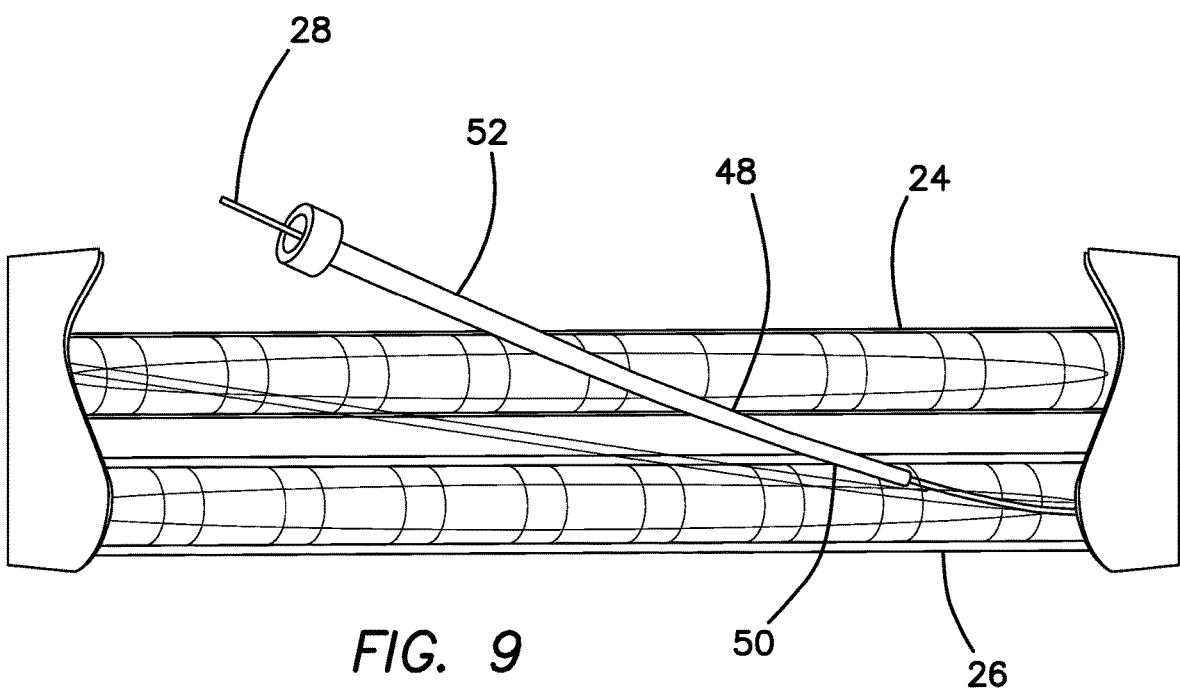
FIG. 9 is a schematic view similar to FIG. 8, wherein the dilator for dilating the vessels at the openings where the anastomosis will be formed has been removed from the procedural site.

Guidewire 28 now provides a track over which the rest of the procedure is performed. First and second vessel openings 48 and 50, respectively must be dilated so that a sheath 52 (FIG. 8) and dilator device 54 (FIG. 10) may have access. FIG. 8 shows a dilator 54 advancing over guidewire 28 to dilate vessel 24 at opening 48 and vessel 26 at opening 50 in anticipation of needing these openings to advance sheath 52 and finally a fistula creation device or catheter 56. The sheath 52 is rotated as it is advanced over the wire 28 to release any tissue that may be caught on the transition between the guidewire and dilator or dilator and outer sheath. Once the sheath 52 is in the artery 26, the dilator 54 is removed, as shown in FIG. 9.

Figure 10:
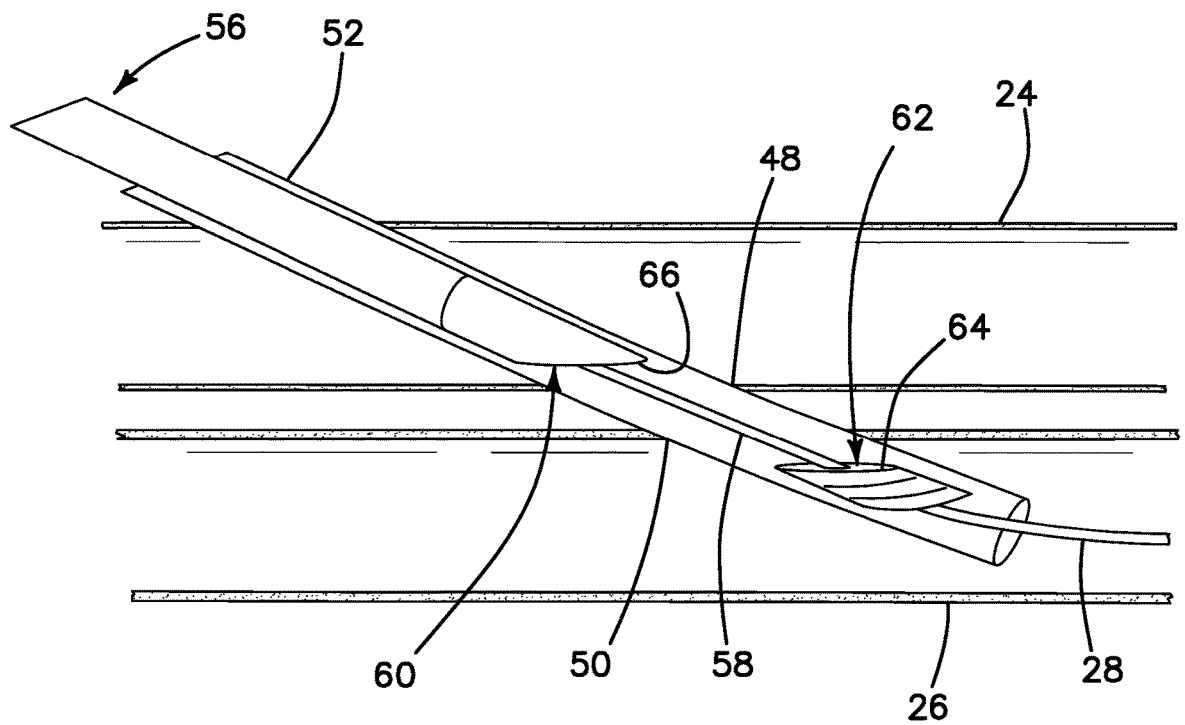
FIG. 10 is a schematic view similar to FIG. 9, wherein a fistula creation catheter has been inserted into the sheath and over the guidewire to the procedural site, according to one representative embodiment.
Figure 11:
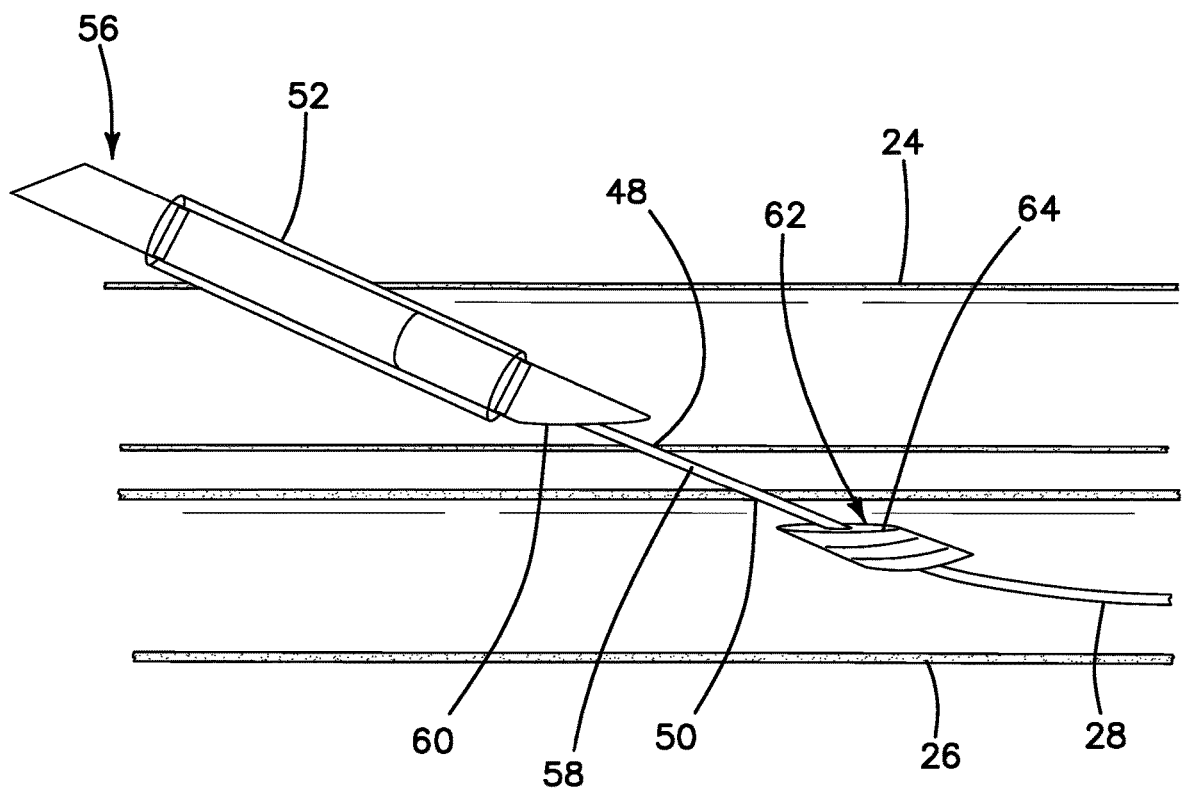
FIG. 11 is a schematic view similar to FIG. 10, wherein the sheath of the device, if the device has a sheath, has been withdrawn from the procedural site.

As shown in FIG. 10, the fistula creation catheter 56 is then inserted into the patient by loading into the proximal end of sheath 52 and over guidewire 28. The catheter 56 is advanced further into the patient until an inner tube or shaft 58 is centered at the anastomosis site. The catheter 56 comprises a proximal member 60 and a distal member 62, joined together by the shaft 58. The catheter 56 is positioned so that that distal member or tip 62 is extended and located in the artery 26. The sheath 52 is then retracted to expose the hook on the proximal end of the distal tip 62, as shown in FIG. 11.

It should be noted, at this juncture, that though the illustrated embodiment includes a sheath 52 and dilator 54, this approach is optional. Other embodiments may be utilized in association with the inventive methods which do not employ a sheath or sheath-based dilator. In such alternative embodiments, one of which is illustrated in FIGS. 14-18, the catheter 56 itself has a tapered distal tip 62 that is capable of tracking over the guidewire and dilating the skin and venous wall directly. In these alternative approaches, once the device is in the vein (first blood vessel) 24, the dilating tip is expanded to a larger peripheral size and advanced into the artery (second blood vessel). Such a dilating tip could comprise expandable structure or even an inflatable balloon.

In still another alternative approach, the dilator 54 may comprise an expandable structure, including an inflatable balloon, disposed on the sheath 52, as shown, or on a shaft or other suitable positioning device.

In certain circumstances, a practitioner may deem the dilation of the openings 48 and 50 using the dilator 54, whether or not the dilator 54 comprises an expandable structure such as an inflatable balloon, or an expandable dilating tip, including inflatable balloon, as discussed above, to be adequate for the purpose of creating a useful fistula, and may determine to dispense with the remaining steps disclosed below. However, generally speaking, cutting and welding the tissue surrounding the dilated openings, as described below, is important for creating a durable and permanent anastomosis of the type desired for the purpose of ongoing hemodialysis access.

At this juncture, except for the limited circumstances just described, wherein dilation of the openings 48 and 50 serves the practitioner's purposes, the distal member 62 is retracted in the artery 26 until the proximal face 64 on the distal member 62 engages the arterial wall and the user feels resistance. Under ultrasound visualization, the user can also see the arterial wall moving when the distal member 62 engages the wall.

Figure 12:
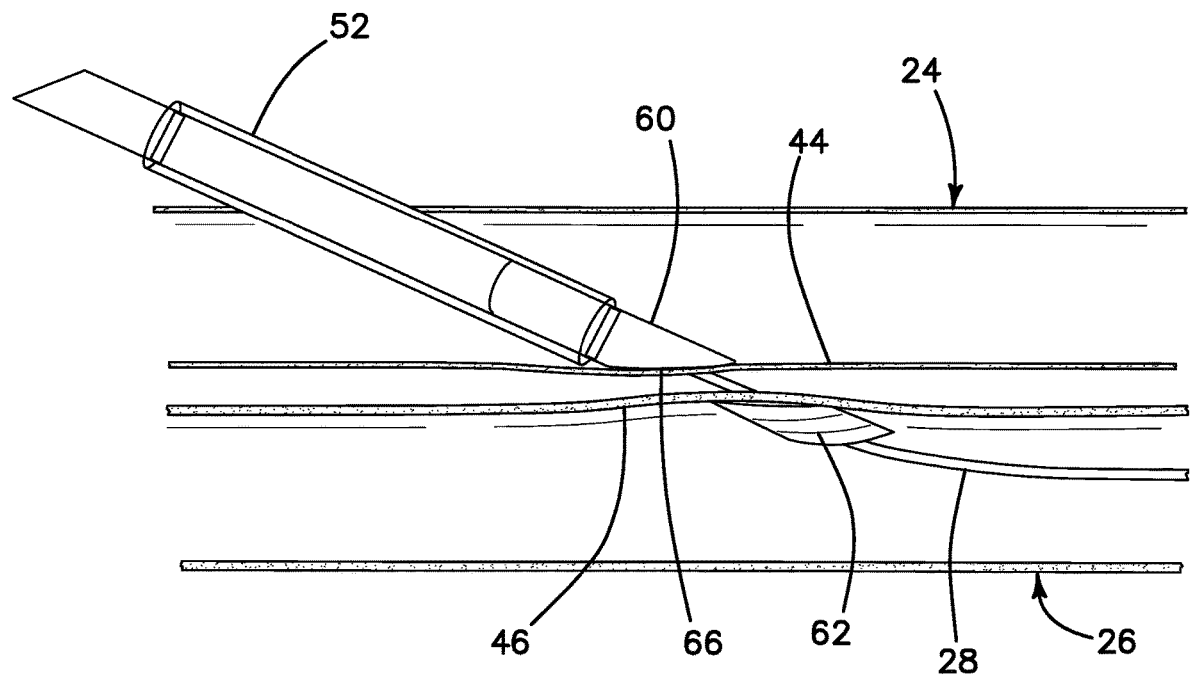
FIG. 12 is a schematic view similar to FIG. 11, wherein the tissue contacting surfaces on the respective distal and proximal members of the device have been brought together to contact, capture, and approximate the tissue walls of each of the first and second blood vessels.

The tissue contacting elements on the distal and proximal members, comprising distal face 66 on the proximal member 60 and proximal face 64 on the distal member 62, are brought together to compress the walls of the vein and artery together. The pressure between the elements is controlled by a spring. This step is illustrated in FIG. 12 and also in FIGS. 16 and 17.

Typically, the tissue captured between the elements 60, 62 measures approximately 0.1 to 0.6 mm thick. If the distance between elements is outside of this range, the power controller (not shown) warns the user that the arterial or venous wall may not have been captured correctly and advises the user to verify positioning. If necessary, the user can open the elements by actuating the inner tube 58 to move the distal member 62 distally again, and then recapture the respective arterial and venous walls.

Figure 13:
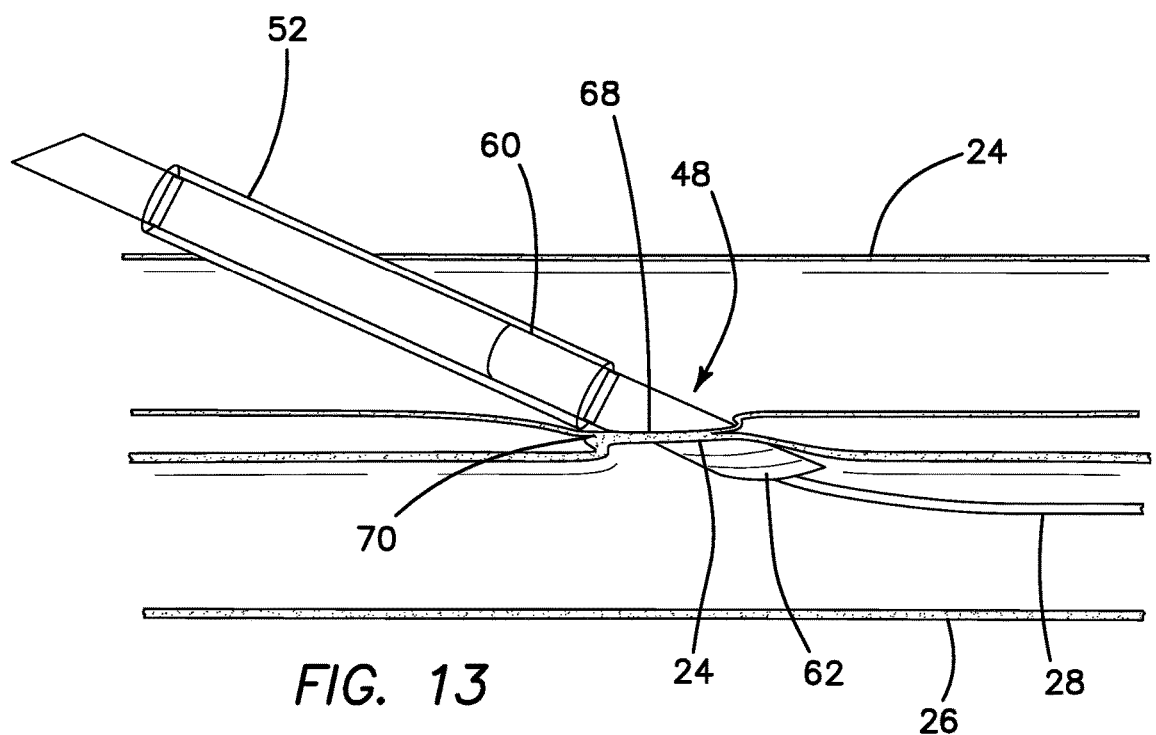
FIG. 13 is a schematic view similar to FIG. 12, wherein heating energy has been applied to the captured tissue to create an orifice between the two adjacent blood vessels.
Figure 14:
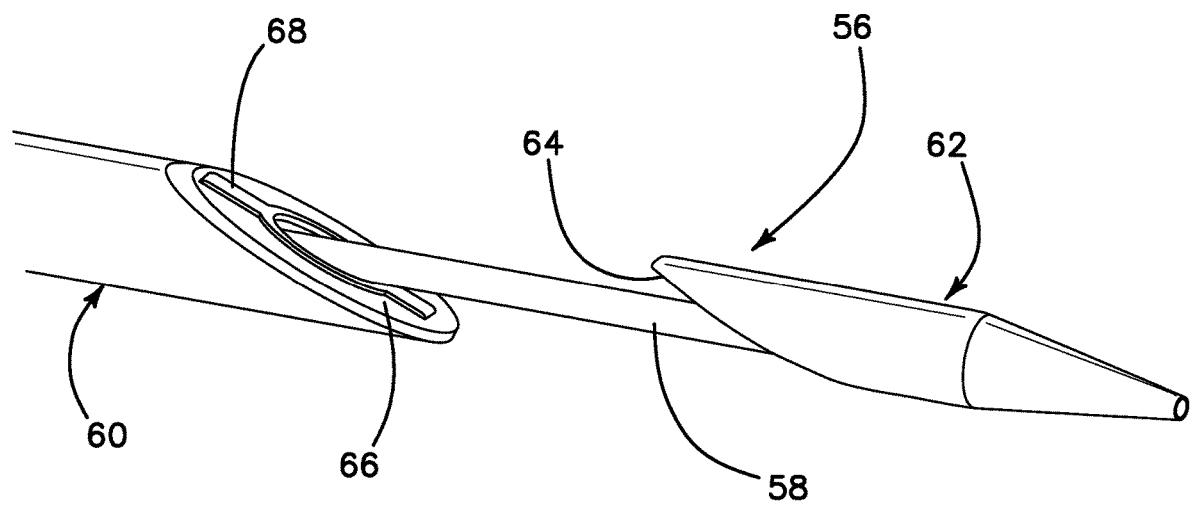
FIG. 14 is an isometric view illustrating another representative embodiment of a fistula creation catheter and dilator which may be used to perform the inventive method.

A heater 68 is disposed on at least one of the proximal and distal faces 64, 66, respectively, and is shown in both FIGS. 13 and 14 on the distal face 66. Direct current is applied to the heater embedded in the proximal venous tissue contacting element. Embedded thermocouples and closed loop temperature control is used to heat to a prescribed temperature, ranging from 200 F to 700 F.

In order to minimize the thermal damage into the surrounding tissues, short pulses of direct current energy are applied to the heating surface 68. Subsequent heating pulses may be triggered on set time intervals or when the temperature of the tissue contacting element cools to a desired temperature. Heating pulses typically range from 0.5 to 3 seconds in length.

Figure 18:
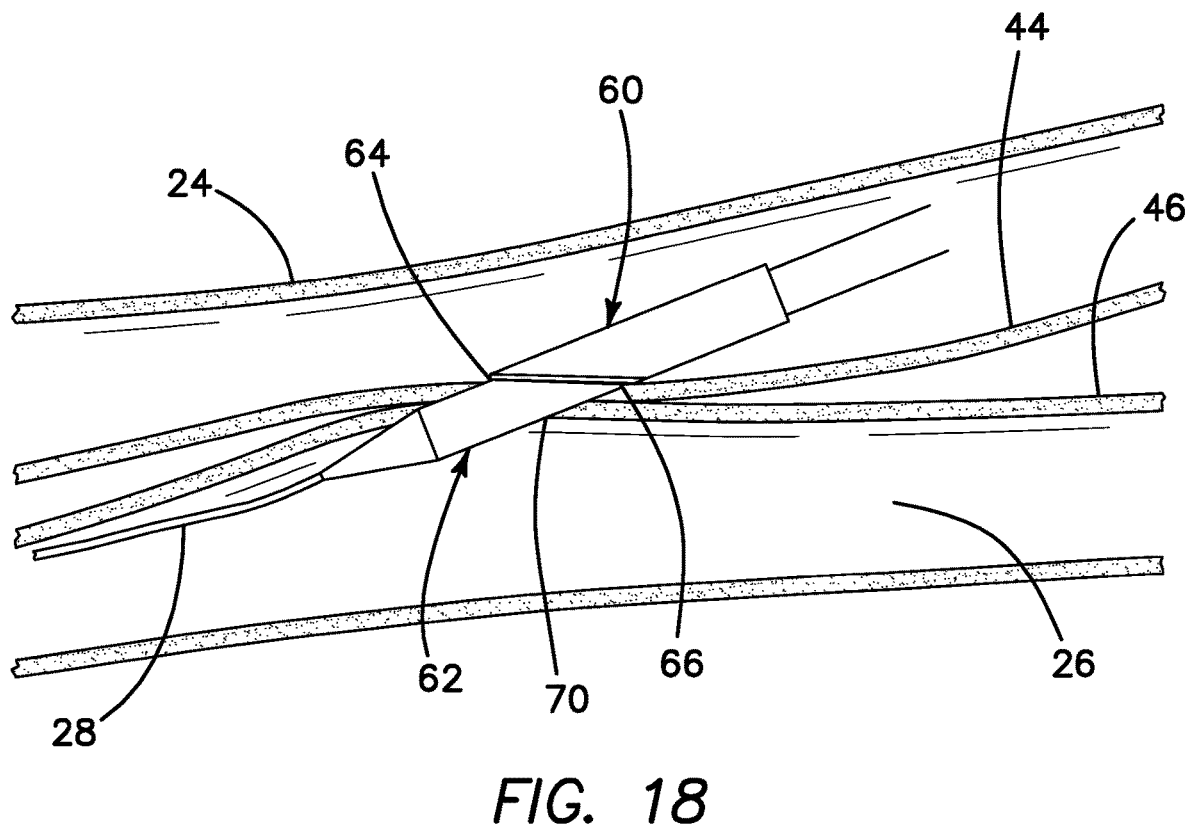

As the heating element or elements heat the proteins in the tissue surrounding the heating element(s), the tissue is denatured and bonds together, forming a seal or weld between the arterial and venous walls. The tissues disposed in between the heated tissue contacting elements are heated in excess of 160 C and is ablated and removed, leaving an orifice 70 between the artery and the vein (FIGS. 13 and 18).

The distance between the tissue contacting elements is monitored during heating. When the elements come into contact with each other, the catheter stops heating.

If required, to aid in the removal of the catheter from the tissue, a short burst of heat is applied to the tissue contacting elements while applying a slight tension on the catheter. The heat causes the tissue surrounding the catheter which may be sticking to release.

Figure 19:
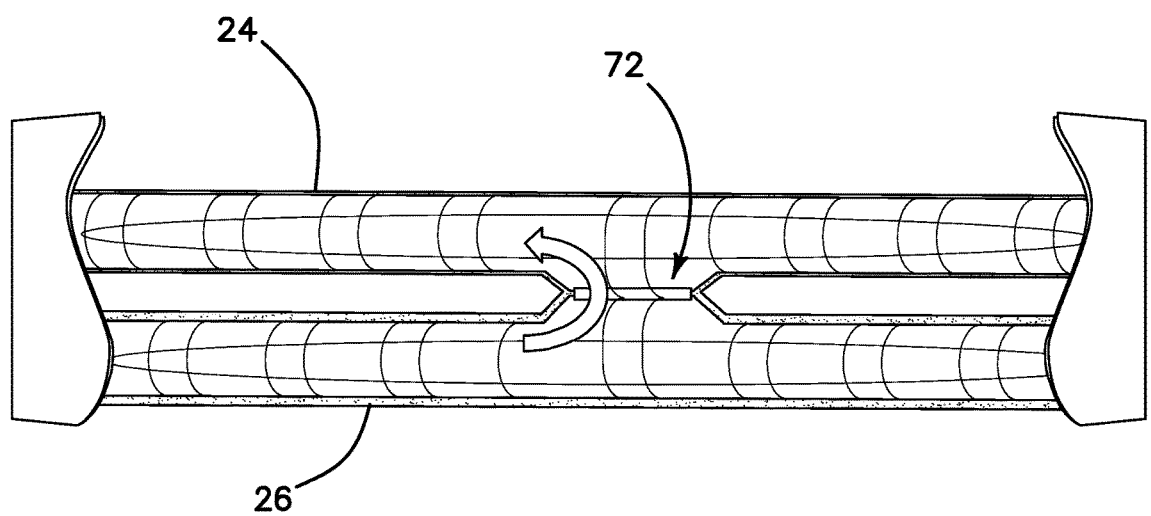
FIG. 19 is a schematic view wherein a fistula has been fully formed and the catheter, whether that illustrated in FIGS. 10-13, that illustrated in FIGS. 14-18, or any other suitable catheter device, has been removed from the procedural site.
Figure 15:
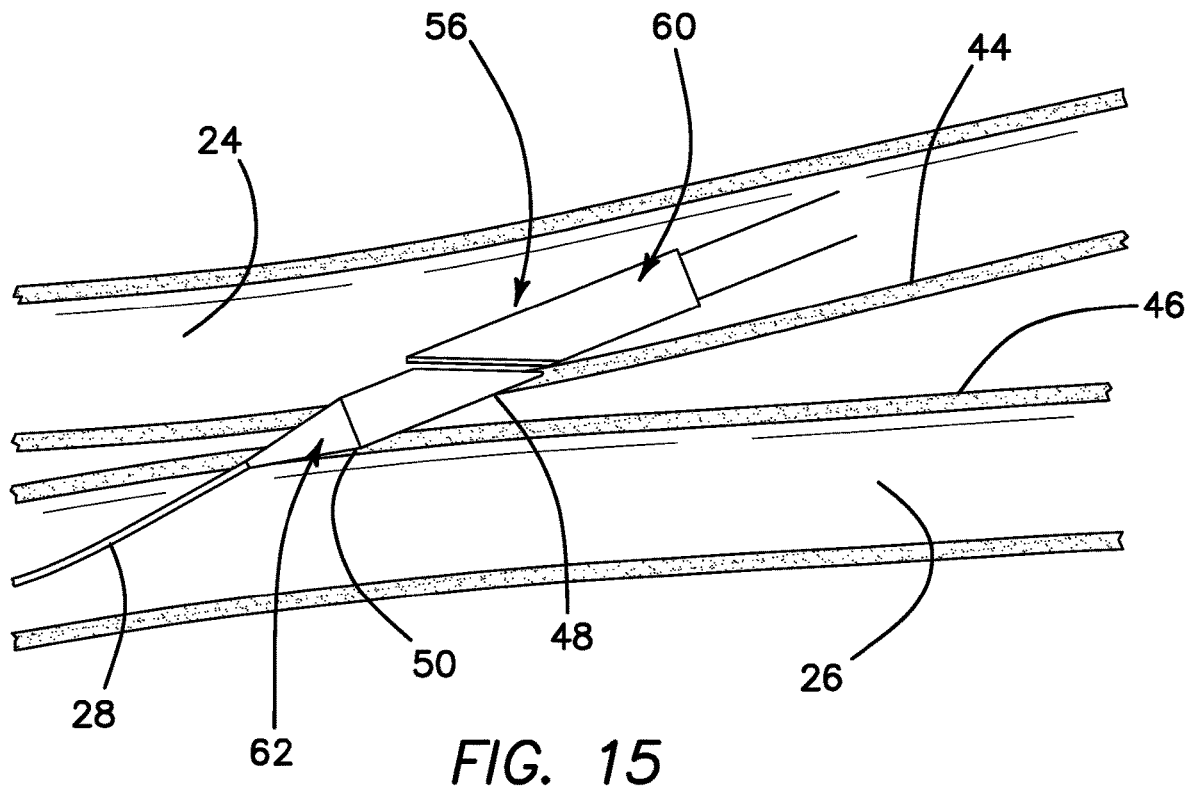
FIGS. 15-18 are schematic views illustrating the use of the embodiment of FIG. 14 in creating an anastomosis according to the methods of the present invention.
Figure 16:
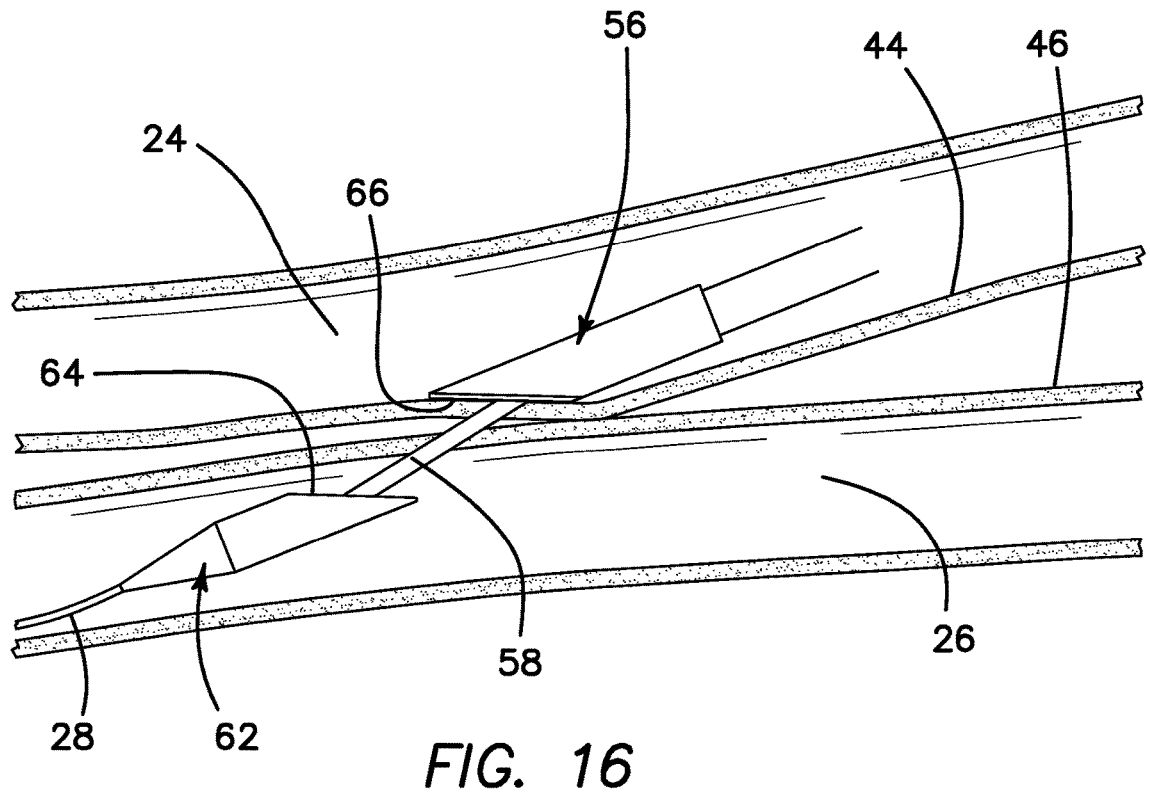
Figure 17:
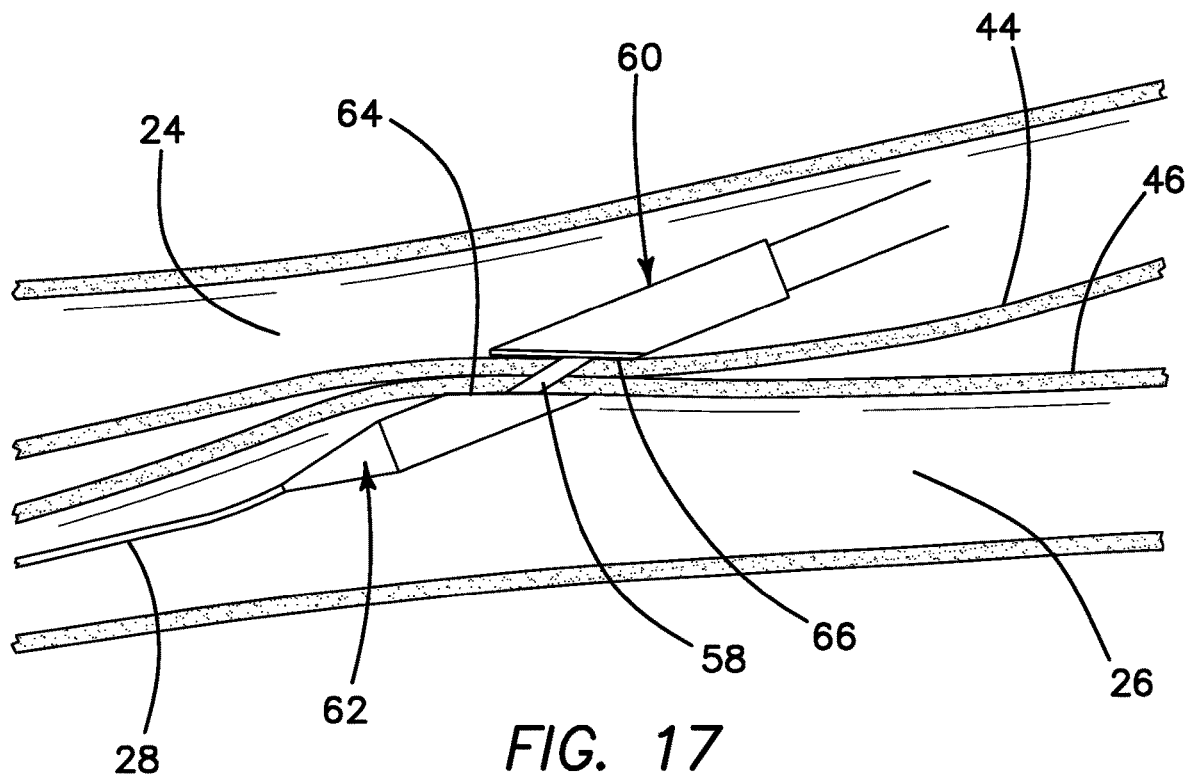

Once the fistula 72 has been fully formed (FIG. 19), using either of the representative embodiments illustrated in FIG. 8-13 or 14-18, or other suitable embodiments of a similar type, the catheter 56 is removed with the guidewire remaining in place in the radial artery and sheath remaining in the vein. Patency of the anastomosis is confirmed using Doppler ultrasound. The flow volume through the fistula can be estimated by measuring the flow in the artery proximal to the anastomosis. For an anastomosis created in the proximal radial artery, the flow in the radial artery may be too turbulent and the brachial artery can be used instead.

If the flow volume is not sufficient to support maturation of the fistula 72, the anastomosis and adjacent DCV can be balloon dilated. To minimize complications related to high flow, which are commonly seen in surgically created fistulas, the catheter is designed so that after creation of the anastomosis flows are approximately 500 ml/min. If additional flow is required, the anastomosis can be balloon dilated.

As soon as immediately after creation of the anastomosis, the anastomosis may be dilated by tracking an angioplasty balloon over the guidewire into the vessel. Under ultrasound visualization the balloon is placed so the distal tip of the balloon is in the artery and the proximal end is in the vein. Position is confirmed as the balloon is inflated and can be deflated and repositioned if needed. Balloon diameters are typically 4 mm-6 mm but can vary as required to achieve the desired flow outcome.

After dilating, the flow volume through the fistula is measured again. If the flow is not sufficient (<500 ml/min) then the anastomosis can be dilated with a larger diameter balloon.

Fistula maturation procedures are important to the proper creation and maintenance of a mature and functional fistula. The following procedures can be performed any time after creation of the anastomosis to accelerate the maturation of the fistula.

Blood flow through the anastomosis can be directed to one or more veins to provide sufficient flow to support dialysis. During open surgical creation of an anastomosis, the veins that are not going to be used for dialysis are typically ligated.

No veins are typically ligated during the percutaneous fistula creation, which allows for multiple veins to have elevated flow rates (pluripotent fistula). If the flow is split between too many vessels, a single outflow vein may not have sufficient flow to support dialysis and flow needs to be directed into the desired vessels for dialysis access. If there are one or more vessels that have potential to be used for dialysis, then banding or surgically creating a flow restriction in the secondary vessel is the preferred option to maintain its patency and conserve the vein for possible use in the future. If the primary vessel that is being used for dialysis subsequently fails, the banded secondary vessel can be surgically opened or undergo dilatation angioplasty to increase the flow for dialysis access. Typical surgical fistulas connect an artery directly to a single vein which limits future potential dialysis access locations, so the inventive methods are a significant advantage.

If the arterial inflow through a fistula is insufficient to support dialysis (<500 ml/min.) in an access vein the size of the anastomosis or outflow vein can be increased by balloon dilation. Because there are minimal side branches in the radial artery, and the blood flow travels from the artery through the anastomosis (see FIG. 13), it is preferred to access the anastomosis with a guidewire through a sheath in the distal radial artery. A dilatation balloon can subsequently be tracked over the guidewire to dilate the anastomosis or outflow vein. A guide catheter can also be place through a sheath in the distal radial artery to allow access to the anastomosis if the anatomy is more tortuous.

In traditional fistulas, typically only a single outflow vein is commonly used for dialysis access. Vessel diameter, depth of vessel below the skin, and flow rate are all evaluated to determine if a fistula is suitable for dialysis access. Kidney Disease Outcomes Quality Initiative (KDOQI) guidelines specify that a vessel should be 6 mm in diameter, <6 mm deep, and have >600 ml/min of flow to be suitable for dialysis. Since a percutaneously created fistula can have multiple outflow vessels, the traditional KDOQI guidelines do not necessarily apply. For example, if two different vessels are being used (one vessel for blood supply, other for blood return) the flow rates can be lower (200-300 ml/min). Also, if the vessels are more superficial, which is typical for veins in the elbow region, the diameters can be less than 6 mm because they are easily visualized and palpated.

Accordingly, although an exemplary embodiment and method according to the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A method for creating a side-to-side anastomosis between first and second blood vessels, comprising:
    identifying an anatomical location in a patient as a procedural site, wherein a distance between the first blood vessel and the second blood vessel is approximately 2 mm or less;
    accessing the procedural site through the deep communicating (perforating) vein (DCV) whereby at least one superficial outflow vessel communicating with the procedural site has a diameter of at least 2 mm;
    measuring a diameter of the at least one superficial outflow vessel to verify that the outflow vessel is free from stenosis, thrombosis or clot, and to ascertain that the outflow vessel is not thickened or diseased;
    creating an opening through a first blood vessel wall and an adjacent second blood vessel wall, the opening comprising a communicating opening between the first blood vessel and the second blood vessel for creating the side-to-side anastomosis;
    dilating the communicating opening to form a fistula; and
    selecting the DCV as the first blood vessel.

2. The method recited in claim 1, the identifying step further comprising selecting the radial artery as the second blood vessel.

3. The method recited in claim 1, the identifying step further comprising selecting the brachial artery as the second blood vessel.

4. The method as recited in claim 1, and further comprising a step of dilating the first blood vessel before the step of creating an opening.

5. The method as recited in claim 4, wherein the dilating step is performed using one of a brachial plexus block (BPB), an axillary block, or a vasodilator drug.

6. The method as recited in claim 1, wherein the step of creating the opening is performed using a needle.

7. The method as recited in claim 1, wherein the step of dilating the communicating opening is performed using a dilator.

8. The method as recited in claim 7, wherein the dilator is expandable to a larger peripheral size in order to effectively dilate the communicating opening.

9. The method as recited in claim 8, wherein the dilator comprises an expandable balloon.

10. The method as recited in claim 1, and further comprising a step of removing tissue to enlarge the communicating opening.

11. The method as recited in claim 10, and further comprising a step of applying heat to tissue surrounding the communicating opening to seal or weld the tissue.

12. The method as recited in claim 11, and further comprising a step pf measuring blood flow volume to determine blood flow volume through the communicating opening, and dilating the communicating opening if the determined blood flow volume is below a predetermined level.

13. The method as recited in claim 12, wherein the dilating step after determining the blood flow volume through the communicating opening is performed using an inflation balloon.

14. The method as recited in claim 1, further comprising:
    determining blood flow volume through the communicating opening; and dilating the communicating opening if the determined blood flow volume is below a predetermined level.

15. The method as recited in claim 14, wherein the predetermined blood flow volume level is approximately 500 ml/min.

16. The method as recited in claim 14, wherein the dilating step after determining the blood flow volume is performed using an inflatable balloon.

17. The method as recited in claim 15, and further comprising a second step of determining the blood flow volume through the communicating opening after the dilating step.

18. The method as recited in claim 17, and further comprising a second step of dilating the communicating opening if the determined blood flow volume obtained during the second step of determining the blood flow volume is below the predetermined blood flow volume level.

19. The method as recited in claim 18, wherein the second dilating step is performed using a larger dilator or longer dilation time than was used to perform the first dilating step.

20. The method as recited in claim 14, and further comprising a step of evaluating secondary outflow vessels downstream from the communicating opening for suitability of use as a future dialysis access point creating a flow restriction in one of the secondary outflow vessels.

* * * * *